United States Patent
Choi et al.

(10) Patent No.: US 8,426,651 B2
(45) Date of Patent: *Apr. 23, 2013

(54) CATALYST COMPOSITION FOR HYDROFORMYLATION AND METHOD FOR PRODUCING ALDEHYDE USING THE SAME

(75) Inventors: Jae Hui Choi, Daejeon (KR); Dong Hyun Ko, Daejeon (KE); Sung Shik Eom, Daejeon (KR); Moo Ho Hong, Daejeon (KR); O Hark Kwon, Daejeon (KR); Dae Chul Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/092,817

(22) Filed: Apr. 22, 2011

(65) Prior Publication Data

US 2011/0201844 A1    Aug. 18, 2011

Related U.S. Application Data

(63) Continuation of application No. PCT/KR2010/000921, filed on Feb. 12, 2010.

(51) Int. Cl.
*C07C 45/50* (2006.01)
*B01J 31/00* (2006.01)

(52) U.S. Cl.
USPC .......................... 568/454; 502/155

(58) Field of Classification Search .................. 568/454; 502/155
See application file for complete search history.

(56) References Cited

U.S. PATENT DOCUMENTS

| | | | |
|---|---|---|---|
| 4,408,078 A | 10/1983 | Van Leeuwen et al. | |
| 4,528,403 A | 7/1985 | Tano et al. | |
| 6,040,483 A | 3/2000 | Olivier et al. | |
| 2005/0119495 A1 | 6/2005 | Zhang et al. | |

OTHER PUBLICATIONS

Mitsuo Matsumoto et al., "Rhodium-Catalyzed Low Pressure Hydroformylation of Higher α-OLEFINS: New, Thermally Stable Rhodium Catalysts by Reaction of RhH(CO)(PPh3)3 With Phosphinous Acids", Journal of Molecular Catalysis, vol. 19, No. 3, Jun. 1, 1983, pp. 365-376, XP55023023.

Duncan J et al., "Iridium (III) Complexes of Diphenylphosphinous Acid and Secondary Phosphites", Journal of the Chemical Society, Dalton Transactions, Chemical Society, Letchworth, GB, Jan. 1, 1983, pp. 1755-1762, XP008150290.

Yu. A. Ustynyuk et al., "Tautomerism of Hydrophosphoryl Compounds and Their Features as Ligands in Metal Complex Catalysis. Quantum-Chemical Simulations by the Density Functional Method", Russian Journal of General Chemistry, vol. 78, No. 4, Apr. 1, 2008, pp. 822-832, XP55023014.

T.R.B. Mitchell, "Oxidative Addition of Dialkylphosphine Oxides and of Alkyl Alkylphosphonites to Iridium(I)", Journal of Organometallic Chemistry, vol. 270, No. 2, Aug. 1, 1984, pp. 245-250, XP55023012.

*Primary Examiner* — Sikarl Witherspoon
(74) *Attorney, Agent, or Firm* — McKenna Long & Aldridge, LLP

(57) ABSTRACT

The present invention relates to a catalyst composition for hydroformylation and a method for preparing aldehydes using the same, wherein the catalyst composition for hydroformylation comprises: a triaryl phosphine ligand; a phosphine oxide or phosphine sulfide ligand having a specific chemical formula; and a transition metal catalyst. The catalyst composition provides high catalyst activity and stability and selectivity to normal aldehydes when used in the hydroformylation for preparing aldehydes from olefins.

19 Claims, No Drawings

CATALYST COMPOSITION FOR HYDROFORMYLATION AND METHOD FOR PRODUCING ALDEHYDE USING THE SAME

THE CROSS-REFERENCE TO RELATED APPLICATIONS

The present application is a continuation application of International Application No. PCT/KR2010/000921, filed Feb. 12, 2010, which claims the benefit of Korean Patent Application No. 10-2009-0011408, filed on Feb. 12, 2009. The disclosures of said applications are incorporated by reference herein.

TECHNICAL FIELD

The present invention relates to a catalyst composition for hydroformylation and a method for preparing aldehydes using the same, and more specifically to a catalyst composition for hydroformylation and a method for preparing aldehydes using the same, in which the catalyst composition for hydroformylation includes a triaryl phosphine ligand; a phosphine oxide or phosphine sulfide ligand represented by a specific Chemical Formula; and a transition metal catalyst.

BACKGROUND OF THE INVENTION

Generally, a hydroformylation that is well known an oxo-reaction is a process for producing linear (normal) and branched (iso) aldehydes, in which one carbon number is increased in olefin, by reacting all sorts of olefins with a synthesis gas ($CO/H_2$) under presence of a metal catalyst and ligand. Otto Roelen in Germany originally discovered the oxo-reaction in 1938, and approximately 840 million ton of all sorts of aldehydes (including alcohol derivatives) are produced and consumed through the oxo-reaction all over the world by 2001 (*SRI report*, November 2002, 682. 700A).

All sorts of aldehydes synthesized from the oxo-reaction are modified to produce acid and alcohol that are aldehyde derivatives through an oxidation or reduction process. Moreover, all sorts of aldehydes synthesized from the oxo-reaction may be modified to produce various acids and alcohols that includes long alkyl group through the oxidation or reduction process after a condensation reaction of aldol, and the like. The alcohols and acids are used as a raw material of solvent, an additive and all sorts of plasticizers, and the like.

A catalyst used for the oxo-reaction is now a type of cobalt (Co) and rhodium (Rh), and N/I (ratio of linear (normal) to branched (iso) isomers) selectivity of aldehyde that is produced is changed by the conditions of operation and type of ligand that is applied. Now, at least 70% of oxo plants in the whole word utilize Low Pressure OXO process that is applied with a rhodium-based catalyst.

Iridium (Ir), ruthenium (Ru), osmium (Os), platinum (Pt), palladium (Pd), iron (Fe), nickel (Ni), and the like may be available to use as a central metal of the oxo catalyst. However, it is known that the order of catalyst activity of metals is Rh>>Co>Ir, Ru>Os>Pt>Pd>Fe>Ni and the like, so that most processes and researches are focused on rhodium and cobalt. Phosphine ($PR_3$; here, R is $C_6H_5$ or $n-C_4H_9$), phosphine oxide ($O=P(C_6H_5)_3$), phosphite, amine, amide, isonitride, and the like may be available to apply as a ligand. However, there are few ligands that can be expected to exceed a triaryl phosphine (TAP) in an activity, stability, and a price of catalyst.

Especially, it is known that rhodium (Rh) metal is used as a catalyst and TPP is used as a ligand in most oxo-processes.

It is known that the Rh catalyst is a very expensive metal so that the triaryl phosphine ligand, such as a triphenyl phosphine ligand, should be applied in the amount of at least 100 equivalents based on the Rh catalyst in order to increase the stability of Rh catalyst. However, the ligand equivalent based on the Rh catalyst is increased in order to increase the stability of the catalyst thereby damaging the activity of catalyst so that high concentration of the ligand is also not preferable to use in a commercial aspect.

Today, the industrial importance of a normal aldehyde is significantly increasing so that a catalyst composition having an excellent stability and high activity of catalyst, and high selectivity to the normal aldehyde is urgently required.

SUMMARY OF THE INVENTION

In order to solve the above problems in prior arts, an object of the present invention is to provide a catalyst composition for hydroformylation and a method for preparing aldehydes using the same, in which the catalyst composition has excellent activity and stability of catalyst, and high selectivity to a normal aldehyde.

The present invention provides a catalyst composition for hydroformylation as a mean for achieving the above object, in which the catalyst composition includes as follows: (a) a triaryl phosphine represented by the following Chemical Formula 1; (b) a phosphine oxide or phosphine sulfide ligand represented by the following Chemical Formula 2 or 3; and (c) a transition metal catalyst represented by the following Chemical Formula 4:

[Chemical Formula 1]

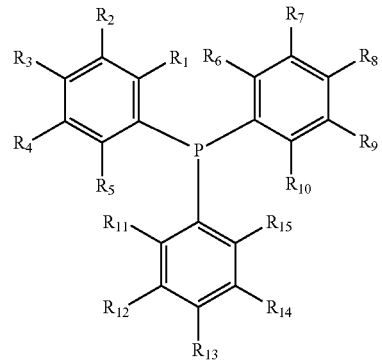

in the above Chemical Formula 1, $R_1$ to $R_{15}$ are each independently hydrogen, substituted or unsubstituted C1 to C5 alkyl group; and substituted or unsubstituted C1 to C5 alkoxy group; and when $R_1$ to $R_{15}$ are substituted by substituents, the substituents are each independently nitro group ($-NO_2$), fluorine (F), chlorine (Cl), bromine (Br) and silyl group ($-SiR$; here, R is hydrogen, alkyl group or alkoxy group,

[Chemical Formula 2]

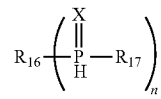

in the above Chemical Formula 2, $R_{16}$ and $R_{17}$ are each independently substituted or unsubstituted C1 to C20 alkyl group; substituted or unsubstituted C5 to C20 cyclo alkyl group or cyclo alkenyl group; substituted or unsubstituted C6 to C36 aryl group; substituted or unsubstituted C1 to C20 hetero alkyl group; substituted or unsubstituted C4 to C36 hetero aryl group; or substituted or unsubstituted C4 to C36 hetero cyclic group, here, hetero alkyl group, hetero aryl group and hetero cyclic group have each independently at least one atom selected from the group consisting of N, O and S;

when $R_{16}$ and $R_{17}$ are substituted by substituents, the substituents are each independently nitro group (—$NO_2$), fluorine (F), chlorine (Cl), bromine (Br), silyl group (—SiR; here, R is hydrogen, alkyl group or alkoxy group), alkoxy group, carboxyl group, carboalkoxy group or C1 to C4 alkyl group;

X is O or S, when X is O, it is a phosphine oxide and when X is S, it is a phosphine sulfide; and n is an integer of 1 or 2,

[Chemical Formula 3]

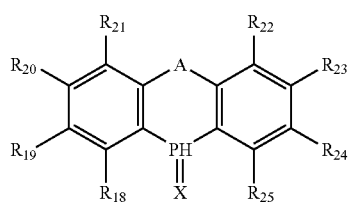

in the above Chemical Formula 3,

A is O, S or amine group (NR'; here, R' is hydrogen, alkyl group, cyclo alkyl group, aryl group, hetero alkyl group or hetero aryl group);

$R_{18}$ to $R_{25}$ are each independently hydrogen, substituted or unsubstituted C1 to C5 alkyl group; substituted or unsubstituted C1 to C5 alkoxy group, carboalkoxy group, aryloxy group, alkylcarbonyl group, amide group (—CONH), nitro group (—$NO_2$), halogen group, cyano group (—CN), silyl group (—SiR; here, R is hydrogen, alkyl group or alkoxy group) or thio group (—SR; here, R is hydrogen, alkyl group or alkoxy group); and X is O or S, when X is O, it is a phosphine oxide and when x is S, it is a phosphine sulfide,

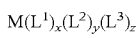  [Chemical Formula 4]

in the above Chemical Formula 4,

M is cobalt (Co), rhodium (Rh) or iridium (Ir);

$L^1$, $L^2$ and $L^3$ are each independently hydrogen, CO, cyclooctadiene, norbornene, chlorine, triphenylphosphine or acetylacetonato; and x, y and z are each independently an integer of 0 to 5, but x, y and z are not 0 at the same time.

The present invention provides a method for preparing aldehydes as a mean for achieving the above object, in which the method includes preparing aldehydes by reacting an olefin-based compound with a synthesis gas ($CO/H_2$) under presence of the catalyst composition according to the present invention.

The present invention relates to a catalyst composition for hydroformylation, in which the catalyst composition includes as follows: (a) a triaryl phosphine represented by the following Chemical Formula 1; (b) a phosphine oxide or phosphine sulfide ligand represented by the following Chemical Formula 2 or 3; and (c) a transition metal catalyst represented by the following Chemical Formula 4:

[Chemical Formula 1]

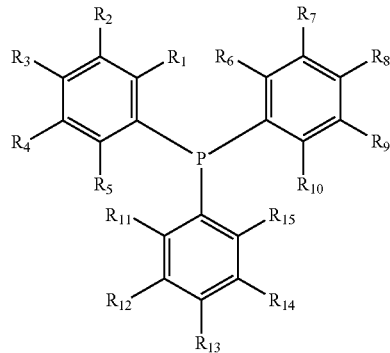

$R_1$ to $R_{15}$ are each independently hydrogen, substituted or unsubstituted C1 to C5 alkyl group; and substituted or unsubstituted C1 to C5 alkoxy group; and when $R_1$ to $R_{15}$ are substituted by substituents, the substituents are each independently nitro group (—$NO_2$), fluorine (F), chlorine (Cl), bromine (Br) and silyl group (—SiR; here, R is hydrogen, alkyl group or alkoxy group),

[Chemical Formula 2]

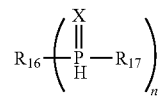

in the above Chemical Formula 2, $R_{16}$ and $R_{17}$ are each independently substituted or unsubstituted C1 to C20 alkyl group; substituted or unsubstituted C5 to C20 cyclo alkyl group or cyclo alkenyl group; substituted or unsubstituted C6 to C36 aryl group; substituted or unsubstituted C1 to C20 hetero alkyl group; substituted or unsubstituted C4 to C36 hetero aryl group; or substituted or unsubstituted C4 to C36 hetero cyclic group, here, hetero alkyl group, hetero aryl group and hetero cyclic group have each independently at least one atom selected from the group consisting of N, O and S;

when $R_{16}$ and $R_{17}$ are substituted by substituents, the substituents are each independently nitro group (—$NO_2$), fluorine (F), chlorine (Cl), bromine (Br), silyl group (—SiR; here, R is hydrogen, alkyl group or alkoxy group), alkoxy group, carboxyl group, carboalkoxy group or C1 to C4 alkyl group;

X is O or S, when X is O, it is a phosphine oxide and when X is S, it is a phosphine sulfide; and n is an integer of 1 or 2,

[Chemical Formula 3]

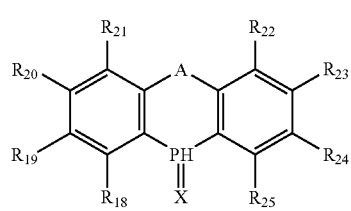

in the above Chemical Formula 3,

A is O, S or amine group (NR'; here, R' is hydrogen, alkyl group, cyclo alkyl group, aryl group, hetero alkyl group or hetero aryl group);

$R_{18}$ to $R_{25}$ are each independently hydrogen, substituted or unsubstituted C1 to C5 alkyl group; substituted or unsubstituted C1 to C5 alkoxy group, carboalkoxy group, aryloxy group, alkylcarbonyl group, amide group (—CONH), nitro group (—NO$_2$), halogen group, cyano group (—CN), silyl group (—SiR; here, R is hydrogen, alkyl group or alkoxy group) or thio group (—SR; here, R is hydrogen, alkyl group or alkoxy group); and X is O or S, when X is O, it is a phosphine oxide and when X is S, it is a phosphine sulfide, $$M(L^1)_x(L^2)_y(L^3)_z \quad \text{(Chemical Formula 4)}$$

in the above Chemical Formula 4,

M is cobalt (Co), rhodium (Rh) or iridium (Ir);

$L^1$, $L^2$ and $L^3$ are each independently hydrogen, CO, cyclooctadiene, norbornene, chlorine, triphenylphosphine or acetylacetonato; and x, y and z are each independently an integer of 0 to 5, but x, y and z are not 0 at the same time.

The catalyst composition for hydroformylation according to the present invention has excellent activity and stability of the catalyst, and high selectivity to a normal aldehyde for hydroformylation of olefin by including a phosphine oxide or a phosphine sulfide represented by the above Chemical Formula 2 or 3 along with a triaryl phosphine compound represented by the above Chemical Formula 1.

Hereinafter, each component of the catalyst composition for hydroformylation according to the present invention will be described in detail.

(a) Triaryl Phosphine Ligand

The catalyst composition for hydroformylation according to the present invention includes a triaryl phosphine ligand represented by the above Chemical Formula 1. Generally, the triaryl phosphine ligand has excellent activity and stability of the catalyst and is relatively cheap as compared with other type of phosphine compounds so that it is in use of most hydroformylations. However, it is known that the triaryl phosphine ligand should be used in the amount of at least 100 equivalents based on the catalyst in order to increase the catalyst-based stability. If the equivalent ratio of ligand/catalyst is increased in order to increase the catalyst-based stability, the activity of the catalyst is decreased in proportion to the increase of above ratio. Thus, the catalyst system that maintains the stability of the catalyst in a high value and also increases the activity of the catalyst is required. The inventors have found the catalyst system that maintains the stability of the catalyst and also increase the activity of the catalyst by applying a phosphine oxide or phosphine sulfide ligand as described as follows along with the triaryl phosphine ligand according to the present invention.

The content of the triaryl phosphine ligand represented by the above Chemical Formula 1 is preferably 0.5 to 200 mole fractions based on 1 mole of the central metal in the transition metal catalyst represented by the above Chemical Formula 4, and more preferably 10 to 150 mole fractions. When the content is less than 0.5 mole fractions, it is possible to not have the reaction of the catalyst due to the lack of proper ligands; and when the content exceeds 200 mole fractions, it is not expected to be favorable in a reaction speed due to excess ligands.

The triaryl phosphine ligand represented by the above Chemical Formula 1 will be described in more detail as follows, but is not limited to the following exemplified compounds:

[Examples of Ligand Represented by Chemical Formula 1]

1)
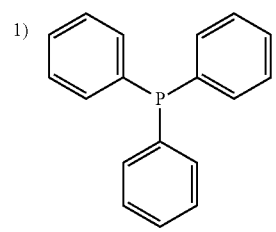
Triphenylphosphine (TPP)

2)
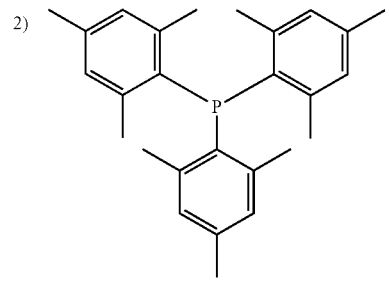
Trimesitylphosphine (TMSTP)

3)
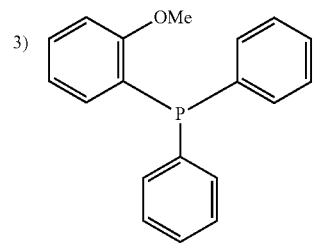
Diphenyl(2-methoxyphenyl)phosphine (DPMPP)

4)
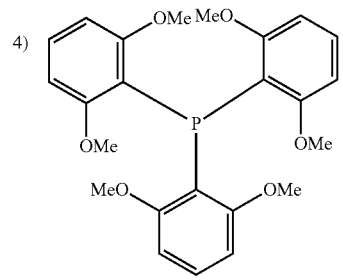
Tris(2,6-dimethoxyphenyl)phosphine (TDMPP)

5)
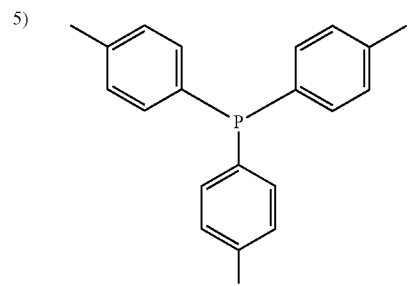
Tri-p-tolylphosphine (TPTP)

TABLE 1 (continued)

[Examples of ligand represented by Chemical Formula 2]

6)
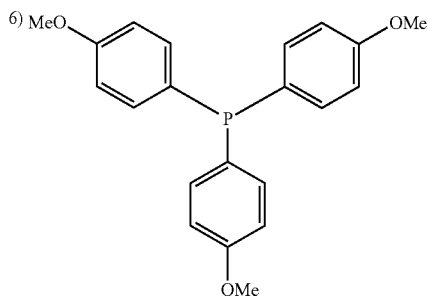
Tris(4-methoxyphenyl)Phosphine
(TMPP)

(b) Phosphine Oxide or Phosphine Sulfide Ligand

The catalyst composition for hydroformylation according to the present invention includes the phosphine oxide or phosphine sulfide ligand represented by the above Chemical Formula 2 or 3 along with the triaryl phosphine ligand represented by the above Chemical Formula 1. The catalyst composition according to the present invention has excellent activity and stability of the catalyst, and high selectivity to a normal aldehyde by including the phosphine oxide or the phosphine sulfide along with the triaryl phosphine ligand. The catalyst composition according to the present invention may include one or combination of the phosphine oxide or phosphine sulfide ligand.

The phosphine oxide or phosphine sulfide ligand represented by the above Chemical Formulas 2 or 3 will be described in more detail as follows, but is not limited to the following exemplified compounds:

TABLE 1

[Examples of ligand represented by Chemical Formula 2]

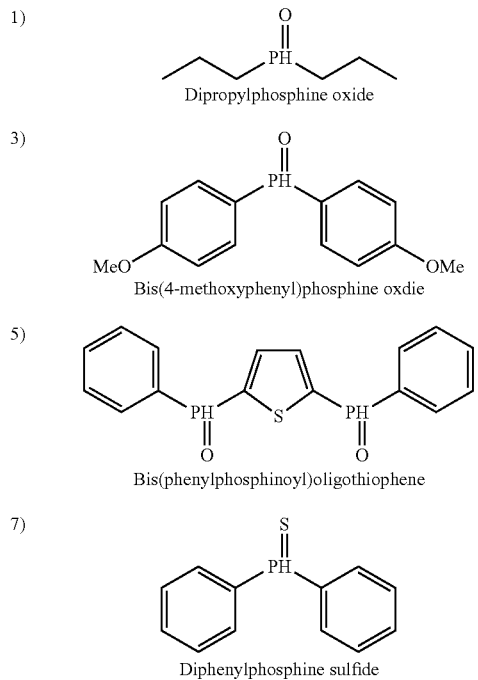

1) Dipropylphosphine oxide

3) Bis(4-methoxyphenyl)phosphine oxdie

5) Bis(phenylphosphinoyl)oligothiophene

7) Diphenylphosphine sulfide

TABLE 2

[Examples of ligand represented by Chemical Formula 3]

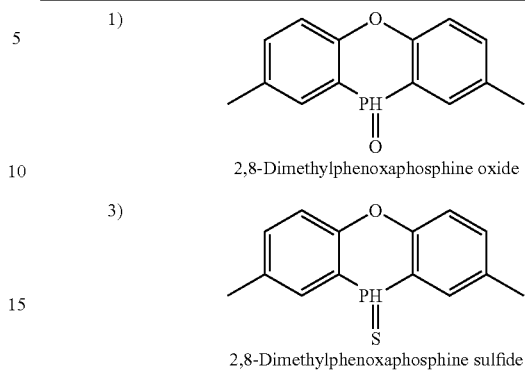

1) 2,8-Dimethylphenoxaphosphine oxide 3) 2,8-Dimethylphenoxaphosphine sulfide

The content of the phosphine oxide or the phosphine sulfide ligand represented by the above Chemical Formula 2 or 3 is preferably 0.5 to 100 mole based on 1 mole of the central metal in the transition metal catalyst represented by the above Chemical Formula 4, and more preferably 1 to 20 mole. When the content is less than 0.5 moles, it is possible to be less effective in the effect appeared by mixing the triaryl phosphine ligand with the ligand; and when the content exceeds 100 moles, it is expected to increase the operation cost due to use an excess ligand without further effects.

(c) Transition Metal Catalyst

The catalyst composition for hydroformylation according to the present invention includes a transition metal catalyst represented by the above Chemical Formula 4.

The transition metal catalyst represented by the above Chemical Formula 4 is not limited in particular, but preferably in the above Chemical Formula 4, $L^1$ is CO, $L^2$ is acetylacetonato, x, y and z are each independently 2, 1 and 0; $L^1$ is CO, $L^2$ is acetylacetonato, $L^3$ is triphenyl phosphine, and all of x, y and z are 1; or $L^1$ is CO, $L^2$ is hydrogen, $L^3$ is triphenyl phosphine, and x, y and z are each independently 1, 1 and 3.

More specifically, the transition metal catalyst represented by the above Chemical Formula 4 is for example, cobaltcarbonyl [$CO_2$ $(CO)_8$], acetylacetonatodicarbonylrhodium [Rh(AcAc)(CO)$_2$], acetylacetonatocarbonyltriphenylphosphinerhodium [Rh(AcAc)(CO)(TPP)], hydridocarbonyltri(triphenylphosphine)rhodium [HRh(CO)(TPP)$_3$], acetylacetonatodicarbonyliridium [Ir(AcAc)(CO)$_2$], hydridocarbonyltri(triphenylphosphine)iridium [HIr(CO)(TPP)$_3$], and the like, and the present invention may use one or combination of at least two of the above them. Acetylacetonatocarbonyltriphenylphosphinerhodium [Rh(AcAc)(CO)(TPP)] is preferably used.

In the transition metal catalyst represented by the above Chemical Formula 4, the content of central metal is preferably 10 to 1000 ppm, and more preferably 50 to 500 ppm based on weight or volume of the catalyst composition. When the content of central metal is less than 10 ppm, the speed of hydroformylation becomes slow so that it is not preferable; and when the content of central metal exceeds 500 ppm, the cost is increased due to the expensive central metal and there is no excellent effect in a reaction speed.

The present invention also relates to a method for preparing aldehydes, in which the method includes obtaining aldehyde by reacting olefin-based compound and a synthesis gas (CO/$H_2$) under presence of the catalyst composition according to the present invention.

Specific components and contents of the catalyst composition according to the present invention are as mentioned above. The catalyst composition according to the present invention can be prepared by dissolving the above components in a solvent. The solvent that can be used for the present invention is not limited, but preferably is a type of aldehyde, such as propane aldehyde, butyraldehyde, pentyl aldehyde, valeraldehyde, and the like, and more preferable is the aldehyde prepared after hydroformylation.

The olefin-based aldehyde used for the method for preparing aldehydes according to the present invention includes the compound represented by the following Chemical Formula 5:

[Chemical Formula 5]

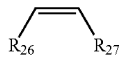

[In the above Chemical Formula 5, $R_{26}$ and $R_{27}$ are each independently hydrogen, C1 to C20 alkyl group, fluorine (F), chlorine (Cl), bromine (Br), trifluoromethyl group (—$CF_3$) or C6 to C20 aryl group with 0 to substituents; and here the substituents of aryl group is nitro group (—$NO_2$), fluorine (F), chlorine (Cl), bromine (Br), methyl group, ethyl group, propyl group or butyl group]

When $R_{11}$ or $R_{12}$ is aryl group in the above Chemical Formula 5, the aryl group is preferably phenyl group.

Specifically, the olefin-based compound represented by the above Chemical Formula 5 is ethene, propene, 1-butene, 1-pentene, 1-hexene, 1-octene, styrene, and the like, and one or combination of at least two of the above compounds may be used.

The synthesis gas used for the method for preparing aldehyde according to the present invention is the mixed gas of CO and hydrogen, and the mixed ratio of CO:$H_2$ is preferably 30:70 to 70:30, more preferably 40:60 to 60:40, and most preferably 50:50 to 40:60, but is not limited thereto. When the mixed ratio of synthesis gas (CO:$H_2$) is less than 30:70 or exceeds 70:30, there is a risk such that the reactivity of catalyst is decreased since the gas that is not used in the reaction is accumulated too much.

The method for preparing aldehyde according to the present invention may use the general known methods with other reaction conditions in addition to the reaction conditions for the catalyst composition according to the present invention.

For the method for preparing aldehyde according to the present invention, the reaction temperature of olefin-based compound and synthesis gas (CO/$H_2$) under presence of the catalyst composition is preferably 20 to 180° C., more preferably 50 to 150° C. and most preferably 65 to 125° C., but is not limited thereto. When the reaction temperature is less than 20° C., there is a problem such that hydroformylation is not proceeded, and when the reaction temperature exceeds 180 t, there is a problem such that the stability of catalyst is largely deteriorated so that the activity of catalyst is reduced. In addition, the reaction pressure is preferably 1 to 700 bar, more preferably 1 to 300 bar and most preferably 5 to 30 bar. When the reaction pressure is less than 1 bar, hydroformylation is not proceeded, and when the reaction pressure exceeds 700 bar, it is not preferable in a industrial aspect because an expensive reactor should be used due to the risk of process explosion without the benefit of specific activity.

Specifically, the method for preparing aldehyde according to the present invention may be roughly shown as the following Reaction Formula 1 or Reaction Formula 2:

[Reaction Formula 1]

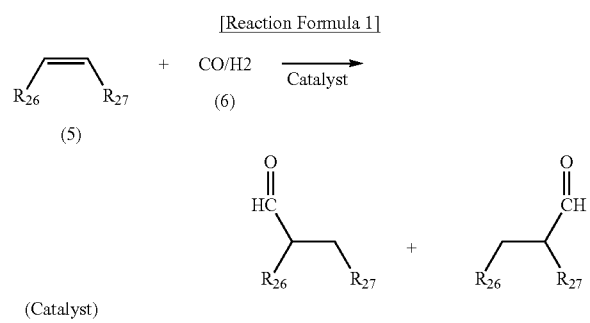
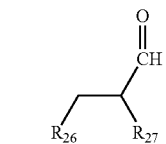
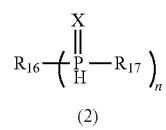

[Reaction Formula 2]

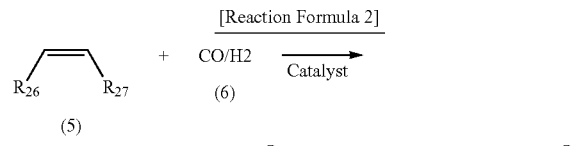
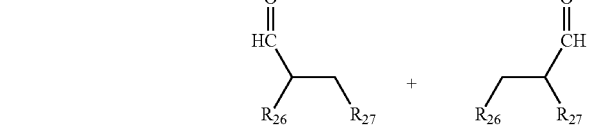
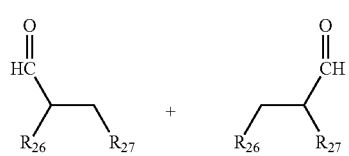
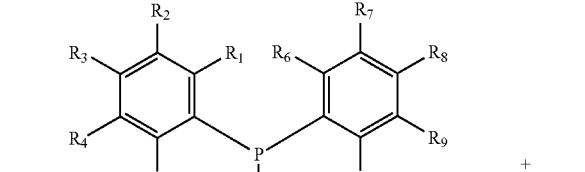
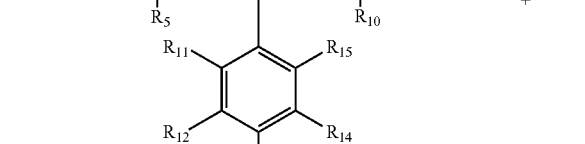

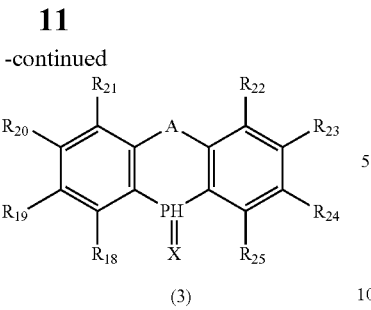

(3)

Firstly, the transition metal catalyst (4), the ligand (1), the ligand (2) or (3) are dissolved in a solvent, such as butyraldehyde or pentyl aldehyde to prepare the mixed solution of the transition metal catalyst and ligand. Since then, the aldehyde can be prepared by proceeding hydroformylation as follows: the olefin-based compound (5) and the synthesis gas of CO and hydrogen (6) along with the above mixed solution were added into a reactor; and the temperature of the reactor is increased and the reactor is pressurized while stirring.

For the catalyst composition for hydroformylation according to the present invention, the ligand includes the compound of phosphine oxide or phosphine sulfide along with triaryl phosphine, and hydroformylation of olefin by using the ligand has high selectivity to a normal-aldehyde and excellent activity and stability of the catalyst. In addition, even if the catalyst composition includes a small amount of phosphine oxide or phosphine sulfide, the catalyst composition has the greatest effect so that there is an advantage such that it can be applied to the oxo-process that uses the triaryl phosphine ligand.

BEST MODES FOR CARRYING OUT THE INVENTION

Hereinafter, the embodiments of the present invention will be described in detail with reference to accompanying Examples and Comparative Examples, but it is only for specifically understanding the present invention and the technical range of the present invention is not limited to Examples.

EXAMPLE

1. N/I Selectivity and Activity of the Catalyst in Hydroformylation

Examples 1 to 13

0.101 g (0.205 mmol) of acetylacetonatocarbonyltriphenylphosphinerhodium{[Rh(AcAc)(CO) (TPP)]:ROPAC} as a catalyst, TPP that is a triaryl phosphine compound (L1), and the following Ligand I, Ligand II, Ligand III, Ligand IV, Ligand V or Ligand VI that are a phosphine oxide or phosphine sulfide compound (L2) that were dissolved in a normal-butyraldehyde solvent, were added to an autoclave reactor of 600 ml volume to be 100 g of the total solution. Propylene and synthesis gas ($CO/H_2$) (mixed ratio of CO and $H_2$=1:1) were injected into the reactor to maintain 6 bar of pressure in the reactor, and reacted for 1.5 hours while stirring.

TABLE 3

| Ligand I | Diphenylphosphine oxide |
| Ligand II | Bis(4-methoxyphenyl)phosphine oxdie |
| Ligand III | Bis(phenylphosphinoyl)benzene |
| Ligand IV | Diphenylphosphine sulfide |
| Ligand V | 2,8-Dimethylphenoxaphosphine oxide |

The transition metal catalyst to the above reaction, the types of ligands, the mole ratio of the ligands to the catalyst, N/I selectivity and the activity of the catalyst were shown in the following Table 4. N/I selectivity is the value that is divided the amount of the normal-butyraldehyde produced from the reaction into the amount of the iso-butyraldehyde produced and the amount of production aldehyde is the value obtained from the gas chromatography (GC) and the solution masses before and after the reaction. The activity of the catalyst is the value that is divided the total amount of aldehyde produced from the reaction into the volume of used catalyst and the reaction time. At this time, the unit of catalyst activity is $gmol_{(BAL)}/L_{(Cat)}/h$.

Comparative Examples 1 to 4

Comparative Examples 1 to 4 were performed with the same methods as Examples 1 to 13 according to the mole rate as disclosed in the following Table 4 by using the triphenylphosphine compound (TPP) as a ligand, and the results were shown in the following Table 4.

Comparative Examples 5 to 7

In order to exclude the effect of the triphenylphosphine compound, Comparative Examples 5 to 7 use 0.053 g (0.205 mmol) of acetylacetonatodicarbonylrhodium {[Rh(AcAc)(CO)2]:Rh(AcAc)} as a catalyst and Ligand I and Ligand IV as a ligand, respectively, were performed with the same methods as Examples 1 to 13 according to the mole rate as disclosed in the following Table 4, and the results were shown in the following

TABLE 4

| Comp. | Transition metal catalyst | L1 | L2 | L1/Rhmol/mol | L2/Rh mol/mol | N/I | Catalyst Activity (gmol$_{(BAL)}$/L$_{(Cat)}$/h) |
|---|---|---|---|---|---|---|---|
| Example 1 | ROPAC | TPP | Ligand I | 115 | 3.7 | 3.0 | 0.93 |
| Example 2 | ROPAC | TPP | Ligand I | 115 | 7.5 | 3.5 | 0.99 |
| Example 3 | ROPAC | TPP | Ligand I | 155 | 7.5 | 4.4 | 0.85 |
| EXample 4 | ROPAC | TPP | Ligand II | 115 | 7.5 | 3.4 | 0.97 |
| EXample 5 | ROPAC | TPP | Ligand II | 155 | 7.5 | 4.3 | 0.83 |
| Example 6 | ROPAC | TPP | Ligand III | 115 | 7.5 | 3.7 | 1.06 |
| Example 7 | ROPAC | TPP | Ligand III | 155 | 7.5 | 4.6 | 0.90 |
| Example 8 | ROPAC | TPP | Ligand IV | 115 | 7.5 | 3.1 | 0.84 |
| Example 9 | ROPAC | TPP | Ligand IV | 155 | 7.5 | 4.0 | 0.72 |
| Example 10 | ROPAC | TPP | Ligand V | 115 | 7.5 | 3.8 | 0.97 |
| Example 11 | ROPAC | TPP | Ligand V | 155 | 7.5 | 4.8 | 0.84 |
| Example 12 | ROPAC | TPP | Ligand VI | 115 | 5 | 4.1 | 0.94 |
| Example 13 | ROPAC | TPP | Ligand VI | 155 | 5 | 4.4 | 0.82 |
| Com. Example 1 | ROPAC | TPP | — | 115 | — | 2.5 | 0.76 |
| Com. Example 2 | ROPAC | TPP | — | 122.5 | — | 2.7 | 0.74 |
| Com. Examp. 3 | ROPAC | TPP | — | 155 | — | 3.6 | 0.65 |
| Com. Example 4 | ROPAC | TPP | — | 162.5 | — | 3.8 | 0.62 |
| Com. Example 5 | Rh(AcAc) | — | Ligand I | — | 3.5 | — | 0.0 |
| Com. Example 6 | Rh(AcAc) | — | Ligind I | — | 7.5 | — | 0.0 |
| Com. Example 7 | Rh(AcAc) | — | Ligand IV | — | 7.5 | — | 0.0 |

L1: Triphenylphosphine compound
L2: Phosphine oxide or phosphine sulfide compound

Examples 14 to 24

0.05 g (0.194 mmol) of acetylacetonatocarbonylrhodium{[Rh(AcAc)(CO)$_2$]:Rh(AcAc)} as a catalyst; TPP, TMSTP, DPMPP, TDMPP, TPTP or TMPP that is a triaryl phosphine compound (L1); and the following Ligand I or Ligand III that is a phosphine oxide compound (L2) that were dissolved in a normal-butyraldehyde solvent, were added to an autoclave reactor of 600 ml volume to be 100 g of the total solution. Propylene, and hydrogen and CO were injected to be 1:0.85:0.75. A condenser with BPR (BACK PRESSURE REGURATOR) was installed in the upper part of the reactor so that a certain part of non-reactive gas may be out of the reactor and H$_2$/CO partial pressure in the reactor can regularly be maintained. While the total pressure was maintained to be 8 bar in the reactor and the solution in the reactor was stirred at 90° C., the reaction was performed for 1.5 hours.

The transition metal catalyst to the above reaction, the types of ligands, the mole ratio of the ligands to the catalyst, N/I selectivity and the activity of the catalyst were shown in the following Table 5.

Comparative Examples 8 to 17

Comparative Examples 8 to 17 were performed with the same methods as Examples 14 to 24 according to the mole rate as disclosed in the following Table 5 by using TPP, TMSTP, DPMPP, TDMPP, TPTP or TMPP that is the triphenylphosphine compound (TPP) as a ligand, and the results were shown in the following Table 5.

Comparative Examples 18 and 19

In order to exclude the effect of the triphenylphosphine compound, Comparative Examples 18 and 19 use Ligand I and Ligand III as a ligand, respectively, were performed with the same methods as Examples 14 to 24 according to the mole rate as disclosed in the following Table 5, and the results were shown in the following Table 5.

TABLE 5

| Comp. | Transition Metal Catalyst | L1 | L2 | L1/Rhmol/mol | L2/Rh mol/mol | N/I | Catalyst Activity (gmol$_{(BAL)}$/L$_{(Cat)}$/h) |
|---|---|---|---|---|---|---|---|
| Example 14 | Rh(AcAc) | TPP | Ligand I | 117 | 7.5 | 12.5 | 1.78 |
| Example 15 | Rh(AcAc) | TPP | Ligand I | 117 | 50 | 12.6 | 1.74 |

TABLE 5-continued

| Comp. | Transition Metal Catalyst | L1 | L2 | L1/Rh mol/mol | L2/Rh mol/mol | N/I | Catalyst Activity (gmol$_{(BAL)}$/L$_{(Cat)}$/h) |
|---|---|---|---|---|---|---|---|
| Example 16 | Rh(AcAc) | TPP | Ligand III | 117 | 7.5 | 13.9 | 1.90 |
| Example 17 | Rh(AcAc) | TMSTP | Ligand I | 117 | 7.5 | 18.2 | 1.69 |
| Example 18 | Rh(AcAc) | TMSTP | Ligand III | 117 | 7.5 | 20.3 | 1.82 |
| Example 19 | Rh(AcAc) | DPMPP | Ligand I | 117 | 7.5 | 15.6 | 1.90 |
| Example 20 | Rh(AcAc) | TDMPP | Ligand III | 117 | 7.5 | 19.4 | 2.23 |
| Example 21 | Rh(AcAc) | TPTP | Ligand I | 100 | 0.5 | 5.0 | 0.98 |
| Example 22 | Rh(AcAc) | TPTP | Ligand I | 100 | 7.5 | 5.7 | 1.08 |
| Example 23 | Rh(AcAc) | TPTP | Ligand I | 100 | 50 | 5.8 | 1.05 |
| Example 24 | Rh(AcAc) | TDMPP | Ligand III | 100 | 7.5 | 5.1 | 0.97 |
| Com. Example 8 | Rh(AcAc) | TPP | — | 58 | — | 7.1 | 1.79 |
| Com. Example 9 | Rh(AcAc) | TPP | — | 117 | — | 9.2 | 1.38 |
| Com. Example 10 | Rh(AcAc) | TPP | — | 123.5 | — | 9.3 | 1.36 |
| Com. Example 11 | Rh(AcAc) | TPP | — | 190 | — | 11.5 | 1.12 |
| Com. Example 12 | Rh(AcAc) | TMSTP | — | 117 | — | 13.8 | 1.30 |
| Com. Example 13 | Rh(AcAc) | TMSTP | — | 123.5 | — | 14.0 | 1.27 |
| Com. Example 14 | Rh(AcAc) | DPMPP | — | 117 | — | 11.5 | 1.49 |
| Com. Example 15 | Rh(AcAc) | TDMPP | — | 117 | — | 13.5 | 1.63 |
| Com. Example 16 | Rh(AcAc) | TPTP | — | 100 | — | 4.9 | 0.83 |
| Com. Example 17 | Rh(Ac | TMPP | — | 100 | — | 4.0 | 0.69 |
| Com. Example 18 | Rh(AcAc) | — | Ligand I | — | 7.5 | — | 0.0 |
| Com. Example 19 | Rh(AcAc) | — | Ligand I | — | 50 | — | 0.0 |
| Com. Example 20 | Rh(AcAc) | — | Ligand III | — | 7.5 | — | 0.0 |

L1: Triarylphosphine Compound
L2: Phosphine Oxide or Phosphine Sulfide Compound

Example 25

0.100 mg (0.390 mmol) of Rh(AcAc)(CO)$_2$ that is a catalyst; 4 ml (255 mmol) of 1-Octene, 0.2 ml of Hexadecane that is a representative material of GC analysis; and TPP that is a triaryl phosphine ligand and Ligand I that is a phosphine oxide compound (L2) according to the mole rate of rhodium as disclosed in the following Table 6 were dissolved in a toluene solvent to be 100 g of the total solution, and then injected to an autoclave reactor of 600 ml volume. The reaction gas that has 1:1 of mole rate of CO:H$_2$ was injected to the solution in the reactor so that the pressure in the reactor was maintained to be 10 bar. The solution in the reactor was stirred at 85 and then the reaction was preformed for 4 hours. After reacting, the reaction solution was analyzed with a gas chromatography (GC) and the results were shown in the following Table 6.

Comparative Examples 21 and 22

The test of the catalyst activity was performed with the same method as Example 25 by using TPP as a ligand, and the results were shown in the following Table 6.

TABLE 6

| Comp. | Transition Metal Catalyst | L1 | L2 | L1/Rh mol/mol | L2/Rh mol/mol | Conversion (%) | Total nonanal (yield (%)) | Fraction of n-nonanal (%) |
|---|---|---|---|---|---|---|---|---|
| Example 25 | Rh(AcAc) | TPP | Ligand I | 117 | 7.5 | 97 | 91 | 90 |
| Com. Example 21 | Rh(AcAc) | TPP | — | 117 | — | 92 | 86 | 80 |
| Com. Example 22 | Rh(AcAc) | TPP | — | 123 | — | 91 | 86 | 82 |

0.101 g (0.205 mmol) of ROPAC, TPP that is a triphenyl phosphine compound (L1), and Ligand I that is a phosphine oxide compound (L2) were dissolved into a normal-butylaldehyde solvent according to the mole rate (L/Rh) of ligand to a metal (Rh) of ROPAC as disclosed in the following Table 7, and then added into an autoclave reactor of 300 ml volume to be 100 g of the total solution. The synthesis gas that has 1:1 of mole rate of $CO:H_2$ was injected in the solution so that the pressure in the reactor was maintained to be 6 bar. The aging test was performed while stirring at 125° C. When the time was reached at the time as disclosed in the following Table 7 after heating, the temperature of the solution was decreased, the inner gas was removed, propylene and mixed gas ($CO/H_2$) were injected to maintain the pressure in the reactor to be 6 bar, and then the reaction was performed for 1.5 hours while stirring at 90° C. The activities of the catalyst that are obtained per each condition were shown in the following Table 7. The values in parenthesis were the relative values of rates of catalyst activities losses according to the time based on 100 of catalyst activity of Fresh catalyst solution that was not performed for the aging test.

Comparative Examples 23 and 24

Except for applying TPP as a ligand, the catalyst composition was prepared by using the same method with the method of Example 26. And then the aging test and the test for catalyst activity were performed and the results were shown in the following Table 7:

TABLE 7

| | | | | L1/Rh | L2/Rh | Catalyst Activity $gmol_{(BAL)}/L_{(Cat)}/h$ (Rate of Catalyst Activity Loss, %) | | | |
|---|---|---|---|---|---|---|---|---|---|
| Comp. | Catalyst | L1 | L2 | mol/mol | mol/mol | Fresh | 2.5 hr | 3.5 hr | 5 hr |
| Example 26 | ROPAC | TPP | Ligand I | 115 | 7.5 | 0.992 (100) | 0.531 (54) | 0.499 (50) | 0.489 (49) |
| Com. Example 23 | ROPAC | TPP | — | 115 | — | 0.763 (100) | 0.425 (56) | 0.391 (51) | 0.377 (49) |
| Com. Example 24 | ROPAC | TPP | | 57 | | 0.992 (100) | 0.396 (40) | 0.358 (36) | 0.328 (33) |

L1: Triphenylphosphine Compound
L2: Phosphine Oxide Compound

Referring to the above Examples and Comparative Examples, Examples 1 to 11, which were applied with the triaryl phosphine ligand, and the phosphine oxide or the phosphine sulfide ligand at the same time, had an excellent activity of catalyst 1.1 to 1.4 times as much, and high selectivity to the normal-aldehyde as compared with Comparative Examples 1 to 4 and 8 to 17, which were applied only with the triaryl phosphine (TAP) under the same conditions. Comparative Examples 3 and 4 had the same selectivity with the selectivity in Examples 1 to 11. However the activities of catalyst in Comparative Examples 3 and 4 were reduced and the used amount of triaryl phosphine ligand was high. In Comparative Examples 5 to 7 and 18 to 20, which were applied only with the phosphine oxide or the phosphine sulfide ligand not the triaryl phosphine ligand, hydroformylations were not proceeded. In addition, Example 26, which was applied with the triaryl phosphine ligand, and the phosphine oxide or the phosphine sulfide ligand at the same time, had excellent activity and stability of catalyst as compared with Comparative Examples 23 and 24, which were applied only with the triaryl phosphine ligand.

What is claimed is:

1. A monodentate phosphine ligand catalyst composition for hydroformylation, comprising:
two types monodentate phosphine ligands of
(a) a triaryl phosphine ligand represented by the following Chemical Formula 1, and
(b) a phosphine oxide or phosphine sulfide ligand represented by the following Chemical Formulas 2 or 3; and
a transition metal catalyst,

[Chemical Formula 1]

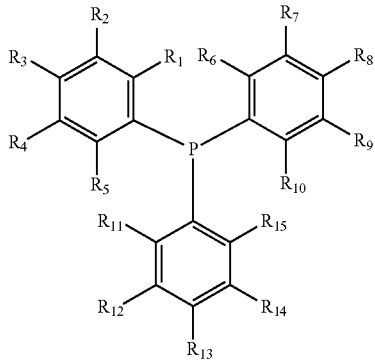

in the above Chemical Formula 1,
$R_1$ to $R_{15}$ are each independently hydrogen, substituted or unsubstituted C1 to C5 alkyl group; and substituted or unsubstituted C1 to C5 alkoxy group; and
when $R_1$ to $R_{15}$ are substituted by substituents, the substituents are each independently nitro group (—$NO_2$), fluorine (F), chlorine (Cl), bromine (Br) and silyl group (—SiR; here, R is hydrogen, alkyl group or alkoxy group);

[Chemical Formula 2]

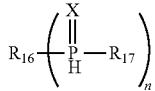

in the above Chemical Formula 2,
$R_{16}$ and $R_{17}$ are each independently substituted or unsubstituted C1 to C20 alkyl group; substituted or unsubstituted C5 to C20 cyclo alkyl group or cyclo alkenyl group; substituted or unsubstituted C6 to C36 aryl group; substituted or unsubstituted C1 to C20 hetero alkyl group; substituted or unsubstituted C4 to C36 hetero aryl group; or substituted or unsubstituted C4 to C36 hetero cyclic group, here, hetero alkyl group, hetero aryl group and hetero cyclic group have each independently at least one atom selected from the group consisting of N, O and S;
when $R_{16}$ and $R_{17}$ are substituted by substituents, the substituents are each independently nitro group (—$NO_2$), fluorine (F), chlorine (Cl), bromine (Br), silyl group (—SiR; here, R is hydrogen, alkyl group or alkoxy group), alkoxy group, carboxyl group, carboalkoxy group or C1 to C4 alkyl group;
X is O or S, when X is O, it is a phosphine oxide and when X is S, it is a phosphine sulfide; and
n is an integer of 1 or 2;

[Chemical Formula 3]

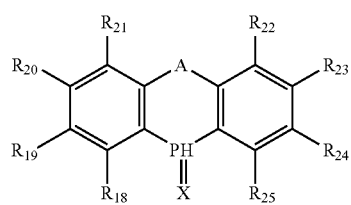

in the above Chemical Formula 3,
A is O, S or amine group (NR'; here, R' is hydrogen, alkyl group, cyclo alkyl group, aryl group, hetero alkyl group or hetero aryl group);
$R_{18}$ to $R_{25}$ are each independently hydrogen, substituted or unsubstituted C1 to C5 alkyl group; substituted or unsubstituted C1 to C5 alkoxy group, carboalkoxy group, aryloxy group, alkylcarbonyl group, amide group (—CONH), nitro group (—$NO_2$), halogen group, cyano group (—CN), silyl group (—SiR; here, R is hydrogen, alkyl group or alkoxy group) or thio group (—SR; here, R is hydrogen, alkyl group or alkoxy group); and
X is O or S, when X is O, it is a phosphine oxide and when X is S, it is a phosphine sulfide.

2. The monodentate phosphine ligand catalyst composition for hydroformylation of claim 1, wherein the (c) transition metal catalyst is represented by the following Chemical Formula 4, $$M(L^1)_x(L^2)_y(L^3)_z$$ [Chemical Formula 4]

in the above Chemical Formula 4,
M is cobalt (Co), rhodium (Rh) or iridium (Ir);
$L^1$, $L^2$ and $L^3$ are each independently hydrogen, CO, cyclooctadiene, norbornene, chlorine, triphenylphosphine or acetylacetonato; and
x, y and z are each independently an integer of 0 to 5, but x, y and z are not 0 at the same time.

3. The monodentate phosphine ligand catalyst composition for hydroformylation of claim 1, wherein the triaryl phosphine is selected from the group consisting of triphenylphosphine, trimesitylphosphine, diphenyl(2-methoxyphenyl)phosphine, tris(2,6-dimethoxyphenyl)phosphine, tri-p-tolylphosphine and tris(4-methoxyphenyl)phosphine.

4. The monodentate phosphine ligand catalyst composition for hydroformylation of claim 1, wherein the triaryl phosphine ligand is 0.5 to 200 mole fractions based on 1 mole of a central metal in the transition metal catalyst.

5. The monodentate phosphine ligand catalyst composition for hydroformylation of claim 1, wherein the phosphine oxide or the phosphine sulfide ligand is 0.5 to 100 moles based on 1 mole of a central metal in the transition metal catalyst.

6. The monodentate phosphine ligand catalyst composition for hydroformylation of claim 2, wherein the transition metal catalyst is at least one selected from the group consisting of cobaltcarbonyl [$Co_2(CO)_8$], acetylacetonatodicarbonylrhodium [Rh(AcAc)($CO)_2$], acetylacetonatocarbonyltri-phenylphosphinerhodium [Rh(AcAc)(CO)(TPP)], hydridocarbonyltri(triphenylphos-phine)rhodium [HRh(CO)$(TPP)_3$], acetylacetonatodicarbonyliridium [Ir(AcAc)$(CO)_2$] and hydridocarbonyltri(triphenylphosphine)iridium [HIr(CO)$(TPP)_3$].

7. The monodentate phosphine ligand catalyst composition for hydroformylation of claim 2, wherein a central metal in the transition metal catalyst is 10 to 500 ppm based on a weight or volume of the catalyst composition.

8. A method for preparing aldehydes, comprising:
obtaining aldehyde by reacting an olefin-based compound and a synthesis gas ($CO/H_2$) in the presence of the monodentate phosphine ligand catalyst composition of claim 1.

9. The method for preparing aldehydes of claim 8, wherein the olefin-based compound comprises a compound represented by the following Chemical Formula 5,

[Chemical Formula 5]

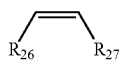

in the above Chemical Formula 5,
$R_{26}$ and $R_{27}$ are each independently hydrogen, C1 to C20 alkyl group, fluorine (F), chlorine (Cl), bromine (Br), trifluoromethyl group (—$CF_3$) or C6 to C20 aryl group with 0 to 5 substituents; and here the substituents of aryl group are nitro group (—$NO_2$), fluorine (F), chlorine (Cl), bromine (Br), methyl group, ethyl group, propyl group or butyl group.

10. The method for preparing aldehydes of claim 8, wherein the olefin-based compound is at least one selected from the group consisting of ethene, propene, 1-butene, 1-pentene, 1-hexene, 1-octene and styrene.

11. The method for preparing aldehydes of claim 8, wherein the mixed ratio of the synthesis gas ($CO:H_2$) is 30:70 to 70:30.

12. The method for preparing aldehydes of claim 8, wherein a temperature of the reaction is 20 to 180° C.

13. The method for preparing aldehydes of claim 8, wherein a pressure of the reaction is 1 to 700 bar.

14. A method for preparing aldehydes, comprising:
obtaining aldehyde by reacting an olefin-based compound and a synthesis gas ($CO/H_2$) in the presence of the monodentate phosphine ligand catalyst composition of claim 2.

15. A method for preparing aldehydes, comprising:
obtaining aldehyde by reacting an olefin-based compound and a synthesis gas ($CO/H_2$) in the presence of the monodentate phosphine ligand catalyst composition of claim 3.

16. A method for preparing aldehydes, comprising:
obtaining aldehyde by reacting an olefin-based compound and a synthesis gas ($CO/H_2$) in the presence of the monodentate phosphine ligand catalyst composition of claim 4.

17. A method for preparing aldehydes, comprising:
obtaining aldehyde by reacting an olefin-based compound and a synthesis gas ($CO/H_2$) in the presence of the monodentate phosphine ligand catalyst composition of claim 5.

18. A method for preparing aldehydes, comprising:
obtaining aldehyde by reacting an olefin-based compound and a synthesis gas ($CO/H_2$) in the presence of the monodentate phosphine ligand catalyst composition of claim 6.

19. A method for preparing aldehydes, comprising:
obtaining aldehyde by reacting an olefin-based compound and a synthesis gas ($CO/H_2$) in the presence of the monodentate phosphine ligand catalyst composition of claim 7.

* * * * *